United States Patent [19]

Farges

[11] Patent Number: 4,805,629
[45] Date of Patent: Feb. 21, 1989

[54] CARDIORESPIRATORY MONITORING APPARATUS

[75] Inventor: Gilbert Farges, Compiegne, France

[73] Assignee: Gradient "Association régie par la loi de 1901", Cedex, France

[21] Appl. No.: 48,367

[22] Filed: May 7, 1987

[51] Int. Cl.$^4$ .......................... A61B 5/02; A61B 5/08
[52] U.S. Cl. .................................... 128/671; 128/700
[58] Field of Search ............... 128/700, 702, 703, 706, 128/708, 710, 696, 671

[56] References Cited

U.S. PATENT DOCUMENTS 3,572,317  3/1971  Hoffmann-La Roche.
4,580,575  4/1986  Birnbaum et al. .................. 128/696

OTHER PUBLICATIONS

Hewlett-Packard Journal, vol. 21, No. 2, Oct. 1969, pp. 12-20, Palo Alto, US; T. C. Horth; "Premonitory heartbeat patterns recognized by electronic monitor" *p. 19, colonne de gauche, lignes 8-24; figure 10*.

Primary Examiner—Francis J. Jaworski
Assistant Examiner—George Manuel
Attorney, Agent, or Firm—Oblon, Fisher, Spivak, McClelland & Maier

[57] ABSTRACT

A cardiorespiratory monitoring apparatus having a sensor for detecting cardiac potentials and a detector for detecting amplitude peaks in the cardiac rate signals which are supplied by the sensor. An apparatus is also included which extracts a respiratory rate representative signal from the cardiac rate signal which is supplied by the detector of the amplitude peaks.

9 Claims, 1 Drawing Sheet

CARDIORESPIRATORY MONITORING APPARATUS

BACKGROUND OF THE INVENTION

1. Field of the Invention

The present invention relates to a cardiorespiratory monitoring apparatus. It applies to the monitoring of the cardiorespiratory rate of any person and particularly the monitoring of the cardiorespiratory rate of an infant, sportsperson, or any other person liable to have a cardiac or respiratory incident or the like.

2. Discussion of Background

It is known that any person having a risk of cardiorespiratory insufficiency must be subject to a quasi-permanent monitoring of the cardiac rate and the respiratory rate. The monitoring of these rates is e.g. even more important for infants, whose sudden unexplained death is now one of the most important causes of mortality before the age of one year. This monitoring must not be neglected, particularly in the case of professional, amateur or occasional sportspersons.

With respect to infants, recent statistics show that in France 20 to 30% of the deaths among infants aged between 1 and 12 months are caused by cardiorespiratory insufficiency. Thus, this insufficiency causes 2000 deaths in each year in France and 10,000 deaths every year in the United States. The pathological causes of this insufficiency are unknown despite a large amount of research. The only possibility of avoiding such deaths is to permanently monitor the cardiorespiratory rate, particularly of infants, when sleeping by day or night. Thus, it is when sleeping, that infants most frequently die. This type of death affects infants apparently in good health and who have never given rise to pediatric disquiet. However, the situation can be saved by e.g. powerful mechanical stimulation leading to the waking up of the infant when such a rate insufficiency is detected, and as a result the infant regains normal control of his or her physiological functions. This is the basis for the interest attached to a cardiorespiratory insufficiency detection apparatus equipped with an alarm.

The population of infants with a cardiorespiratory risk is estimated in the following way:

infants having already suffered a cardiorespiratory accident and who have been saved in extremis, brothers and sisters of an infant less than one year old who has already suffered a cardiorespiratory incident, certain premature infants.

Infants at risk having no major pathological symptom cannot be hospitalized for one year and are therefore monitored at home by cardiorespiratory monitoring equipment. It is estimated that one infant in twenty subject to such risks is monitored in this way at home.

This small proportion is due to the fact that the cardiorespiratory monitoring equipment at present on the market and which is of a reliable nature is very onerous. In addition, the health or insurance organizations do not systematically assume responsibility for the costs of purchasing and maintaining such equipment, which makes the position difficult for medical teams and societies dealing with this problem. The medical body is very reticent regarding monitoring at home. Thus, existing equipment is voluminous, heavy and not very practical. Such equipment constitutes a pathological disturbance for the family using it. These remarks concerning infants are also applicable to persons who may be subject to a cardiac or respiratory incident. Cardiorespiratory monitoring equipment is onerous and cannot be permanently supplied to large numbers of patients having cardiac or respiratory incident risks.

Finally, for all other persons appearing to be in good health and who e.g. engage in amateur sports, cardiorespiratory monitoring can be useful, particularly in the case of major exertion. The presently known cardiorespiratory monitoring equipment is excessively large and onerous to permit such monitoring when force is being exerted.

The most highly developed known cardiorespiratory monitoring apparatuses are of very varied type. The most widely used and reliable apparatus has a sensor with three electrodes fixed to the chest of the person being monitored. One of the electrodes serves as a voltage reference. The heart rate is obtained on the basis of electric potential signals from the heart, taken between the two other electrodes, whereas the respiratory rate is obtained by detecting the amplitude variation of a high frequency, low intensity electric current injected through the chest by these same electrodes. Thus, respiratory movements lead to electrical impedance changes within the chest due to variations in the volume of the organs within the same and, according to Ohm's law, if a constant current is injected across a variable impedance, the voltage at the terminals thereof also varies. The signals representing the respiratory and heart rate are mixed at the output of the sensor. Filtering means make it possible to extract on the one hand signals representing the heart rate and on the other signals representing the respiratory rate. A frequency analyser makes it possible to determine the value of the frequency of the signals representing the heart rate (pulse signals). This frequency analyser is connected to a threshold analyser making it possible to release or give an alarm when the frequency of the heart rate signals is outside predetermined high and low frequency thresholds.

The signals representing the respiratory rate obtained at the output of the filtering means are also applied to a detector, which gives an alarm when the amplitude or frequency of the respiratory rate signals is outside a predetermined amplitude or frequency range.

This type of apparatus suffers from a major disadvantage. When a person stops breathing, the stoppage of the heart does not occur simultaneously and the chest, which is subject to the pulsations of the heart, is consequently subject to non-negligible internal movements. These heart movements lead to a variation in the internal impedance of the chest and consequently the amplitude of the voltage representing the respiratory rate perceived by the electrodes of the sensor, so that at the output of the filtering means signals comparable to those of the respiratory rate are obtained, whereas in fact respiration has completely stopped. Thus, as a function of the position of the electrodes and the sensitivity regulation, in the case of a respiratory stoppage no alarm is given. The alarm is only given when the heart has almost stopped beating or has excessively slowed down, so that the alarm is often given too late.

As stated hereinbefore, to this major disadvantage of such an apparatus is added its very high price, its very large volume, as well as the difficult settings for the sensitivity thresholds of the respiratory rate.

SUMMARY OF THE INVENTION

The present invention aims at obviating these disadvantages and in particular at providing a cardiorespiratory monitoring apparatus in which is used a sensor having two or three electrodes, but in which the signals representing the respiratory rate are not obtained separately from the signals representing the heart rate and are instead extracted from the heart rate signals.

This obtaining of respiratory rate signals from heart rate signals has the important advantage, as will be shown hereinafter, of ensuring a more reliable monitoring and particularly of bringing about the triggering of an alarm even when, with respiratory movements stopped, the heart continues to beat. The apparatus according to the invention also has the advantage of small dimensions, portability and autonomy, without representing any problem to the person carrying it. Its cost is very low and its electrical safety high, because no current is injected into the organism.

The invention relates to a cardiorespiratory monitoring apparatus comprising a sensor for electric cardiac potentials, a detector connected to an output of the sensor for detecting amplitude peaks in the signal supplied by the sensor and characterized in that it also comprises means connected to the output of the amplitude peak detector for extracting a signal representing the respiratory rate from the signal supplied by said amplitude peak detector.

According to another feature, the apparatus also comprises a detector of the amplitude threshold of the respiratory rate signal or at least one frequency threshold of the respiratory rate signal, connected to an output of the means for extracting the signal representing the respiratory rate, an output of said amplitude threshold or respiratory rate frequency detector being connected to an alarm in order to trigger the latter when the amplitude of the signal representing the respiratory rate is outside a range of predetermined amplitudes around the amplitude threshold and/or when the frequency of the respiratory rate signal is outside a range of predetermined frequencies around the frequency threshold and/or when the value of the product of the amplitude of the respiratory rate signal by the period of said signal is outside a range of predetermined values around the value representing the threshold of said product.

According to another feature, the means for extracting a signal representing the respiratory rate comprise a sample and hold circuit connected to the output of the amplitude peak detector and a filter connected to an output of the sample and hold circuit, in order to extract the mean component from the signal supplied by the sample and hold circuit, said mean component being said signal representing the respiratory rate supplied by an output of the filter constituting the output of the extraction means.

According to another feature, the means for extracting a respiratory rate signal are of the digital type.

According to another feature, the apparatus also comprises a frequency analyser connected to the output of the amplitude peak detector and to the alarm for determining the frequency of the detected peaks, said frequency representing the heart rate, a detector of at least one heart rate frequency threshold connected to an output of the analyser for supplying a signal for releasing the alarm when the frequency determined by the analyser is outside a predetermined frequency range around said heart rate frequency threshold.

According to another feature, the amplitude threshold or respiratory rate frequency detector comprises means for delaying the triggering of the alarm.

According to another feature, the frequency analyser is of the digital type.

According to another feature, the heart rate frequency threshold detector has means for delaying the triggering of the alarm.

According to another feature, the sensor comprises at least two electrodes preferably located in the vicinity of the heart.

According to another feature, the sensor has a third reference electrode.

According to another feature, the amplitude peak detector is connected to means for extracting the respiratory rate signal and/or to the frequency analyser by electrical conductors or by wire-less transmission means.

BRIEF DESCRIPTION OF THE DRAWINGS

The invention will be better understood from the description given hereinafter relative to the drawings, wherein show.

DETAILED DESCRIPTION OF THE PREFERRED EMBODIMENT

Figure 1:
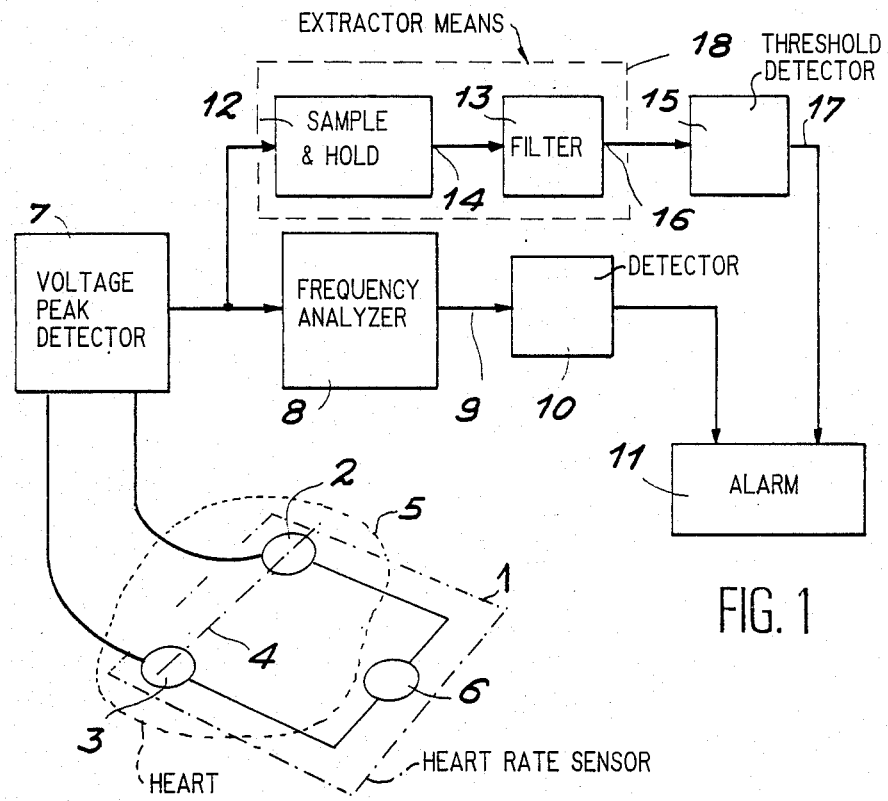
FIG. 1 Diagrammatically a cardiorespiratory monitoring apparatus according to the invention.

The apparatus shown diagrammatically in FIG. 1 comprises a heart rate sensor 1 having two electrodes 2, 3 placed on the chest of the person in the vicinity of the heart 5 and preferably in the vicinity of the electrical axis 4 thereof and a reference electrode 6. In known manner, cardiac pulsations cause periodic potential difference variations between electrodes 2 and 3. These periodic variations are voltage amplitude peaks appearing between the two electrodes 2, 3. The frequency of these voltage peaks represents the heart rate. The apparatus also comprises a voltage peak detector 7 making it possible to detect voltage peaks in signals supplied by the sensor. This apparatus also comprises a frequency analyser 8 for determining the frequency of pulse signals supplied by detector 7. The frequency of these signals is supplied in analog or digital form to an output 9 of frequency analyser 8. This output is connected to the input of an analog or digital detector 10 of the frequency threshold of the pulse signals representing the heart rate. The output of detector 10 is connected to an alarm 11. Detector 10 can have means for delaying the release of the alarm 11 (not shown in the drawing). This alarm is released when the frequency measured by analyser 8 is outside a predetermined frequency range around the frequency threshold of the heart rate signals. Outside said range, the heart rate is considered as being abnormal. These limits can be fixed around the threshold, either by a circuit within the detector 10, or by a circuit within the alarm 11.

According to the invention, the apparatus also comprises means 18 connected to detector 7 for extracting a signal representing the respiratory rate from the signal supplied by the detector.

In an embodiment of the analog type, the extraction means 18 comprise a sample and hold circuit 12 connected to the output of the detector 7 for the amplitude peaks of the heart rate signals. A filter 13 is connected to an output 14 of the sample and hold circuit 12 for extracting, in the manner to be shown hereinafter, the mean component from the signal supplied by said sample and hold circuit. This signal represents the respiratory rate. A threshold detector 15 is connected to output 16 of filter 13. One output 17 of said detector 15 is connected to the alarm 11. This detector makes it possible to trigger alarm 11 when the amplitude of the signal representing the respiratory rate is outside a range of predetermined amplitudes around a predetermined amplitude threshold and/or the frequency of the respiratory rate signal is outside a range of predetermined frequencies around a predetermined frequency range and/or when the value of the product of the amplitude of the respiratory rate signal by the period of said signal is outside a range of predetermined values around a predetermined threshold value of said product. These ranges of amplitude, frequency or product values can be fixed by a circuit within detector 15 or alarm 11.

In a digital embodiment, the extraction means 18 can be constituted by a microprocessor connected to a memory containing a program for processing heart rate signals supplied by detector 7, previously converted into digital signals, by an input converter of the microprocessor. This processing program is not described in detail here, but makes it possible to extract from the heart rate signals, a signal which represents the respiratory rate, as will be shown hereinafter. It should also be noted that the connections between detector 7 and the extraction means 18 and/or between said detector and frequency analyser 8 can be connections by conductors or wire-less transmission means.

Frequency analyser 8, detectors 10 and 17 and alarm 11 can be of an analog or digital type. Finally, recording means of an analog or digital type, as a function of the chosen embodiment, can be connected to the output of any random component of the apparatus, in order to permit the recording and study of the analog or digital signals supplied by each of these components.

Figure 2:
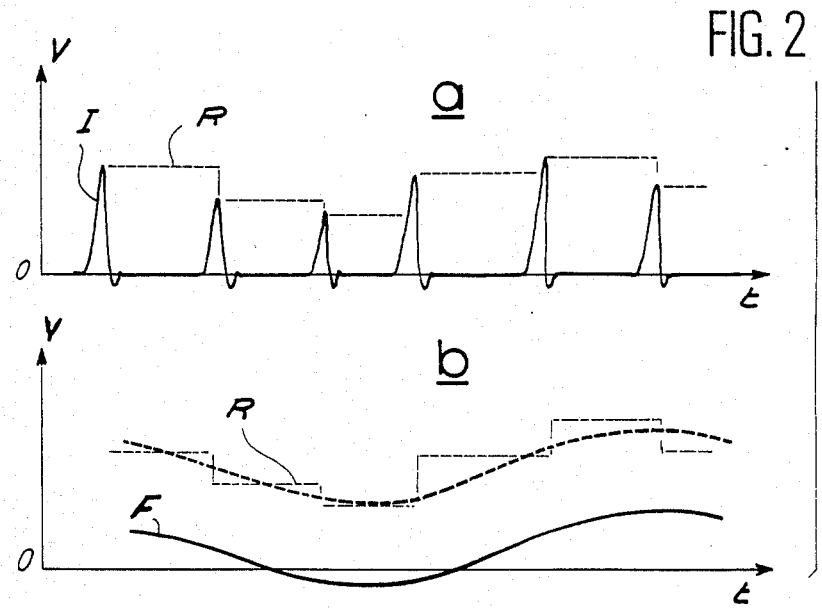
FIG. 2 Diagrammatically at (a) and (b) graphs of different signals obtained in the apparatus according to the invention and which provide a better understanding of the operation of the apparatus.

FIG. 2 diagrammatically shows diagrams or graphs of certain signals obtained in the apparatus according to the invention. Graph (a) shows at I pulse signals obtained at the output of peak detector 7. These pulse signals make it possible to determine the heart rate, because their frequency corresponds to that of the pulsations or beats of the heart. The amplitude of each pulse I is dependent on the different orientations of the heart, when the latter oscillates in the chest as a result of respiratory movements. Thus, when the respiratory movements stop and the heart continues to beat for a few minutes more, the amplitude of pulses I becomes constant, because the heart is no longer subject to any oscillation. The detection of the amplitude variations of pulses I representing the heart rate is consequently very important in the detection of the respiratory rate. As stated hereinbefore, the heart rate is determined by a frequency analyser and, when this rate is outside a range of predetermined frequencies around a threshold, the alarm is given.

The respiratory rate is determined in the following way in the analog embodiment. The signals supplied by peak detector 7 are applied to a sample and hold circuit 12 controlled at the instant of maximum amplitude. This sample and hold circuit makes it possible to obtain on an output 14, signals representing ranges, such as is shown at R in graph (a) of FIG. 2. The structural and operational details of this sample and hold circuit will not be described in detail here, because such a circuit is well known in the art. This sample and hold circuit makes it possible to obtain voltage ranges V between two successive pulses I by holding the voltage read at the input at the time of sampling, the amplitude of the voltage between two pulses being dependent at the output of the sample and hold circuit on the amplitude of the pulse preceding and the amplitude of the pulse following each sampling operation.

The signals R obtained at the output 14 of sample and hold circuit 12 are applied to an averaging filter 13 supplying at its output 16 a respiratory rate signal F, as shown in graph (b) of FIG. 2. This signal F represents the mean amplitude of the output signal of the sample and hold circuit around the voltage zero. When a respiratory stoppage occurs, signal F becomes flat and equal to zero and is subject to no misleading disturbance on the part of the heart, unlike in known cardiorespiratory monitoring apparatuses. Signals R and F have the same frequency and period or cycle.

Threshold detector 15, which is connected to the output 16 of filter 13, gives the alarm 11 under the conditions indicated hereinbefore. This threshold detector is not described in detail here and can be constituted in known manner by a Schmitt trigger-type circuit connected to the output of filter 13 and by a time lag circuit connected to one output of the trigger. The time lag circuit supplies at output 17 a logic level 1 signal, e.g. when the Schmitt trigger permanently supplies pulses resulting from amplitude variations of signal F. This time lag circuit supplies a logic level zero signal when the Schmitt trigger stops supplying pulses, i.e. when signal F stops having adequate amplitude variations. This logic level zero signal makes it possible to trigger alarm 11. In the case of detecting frequencies of the signal representing the respiratory rate, the Schmitt trigger is associated with a frequency threshold detector.

In the case of detecting values of the product of the amplitude of the respiratory rate signal by the period of said signal, the Schmitt trigger is associated with a multiplier circuit and a detector of the threshold of the value of said product.

In a digital embodiment of the apparatus, extraction circuit 18 having a processing microprocessor also directly supplies a digital signal equivalent to signal F or R. The thresholds of the amplitude or frequency or the values of the amplitude-frequency products are then digitally determined.

The apparatus described hereinbefore makes it possible to obviate the disadvantages of known apparatuses. The alarm is triggered without ambiguity, either because the heart rate is outside the predetermined frequency limits, or because the amplitude of the respiratory rate signal is outside the predetermined limits for an excessive time, or because the value of the product of the amplitude of the respiratory rate signal by the period of said signal is outside the predetermined limits. Thus, this product represents the ventilatory capacity of the person. These inadequacies or abnormalities can also occur simultaneously and in this case threshold detector 15 is appropriately designed.

The apparatus is autonomous and can be carried by the person being monitored. It can be energized by batteries and its manufacturing cost is very low.

With regards the amplitude of the heart rate signal, it is generally when said amplitude drops below a predetermined threshold that the alarm has to be triggered. In certain cases of respiratory insufficiency, for which the inadequately ventilated patient draws in air very strongly, it may be useful to also trigger the alarm when the amplitude of the respiratory rate signal becomes excessive.

It is also possible to fix two heart rate signal frequency thresholds outside of which the alarm is given. The low frequency threshold corresponds to an excessively low heart rate (bradycardia), whereas the high frequency threshold corresponds to an excessively high heart rate (tachycardia).

I claim:

1. A cardiorespiratory monitoring apparatus comprising:
   a sensor for sensing electric cardiac potentials and outputting signals which include beat pulses;
   a detector connected to the output of said sensor for detecting heart beat pulses in said signals supplied by said sensor; and
   extraction means connected to the output of said detector of heart pulses for extracting a signal representing respiratory rate from said signals supplied by said heart beat pulses detector, wherein said respiratory rate signal is supplied as an output of said extraction means, said means for extracting a signal representing the respiratory rate comprising a sample and hold circuit connected to the output of said heart pulses detector and a filter connected to the output of said sample and hold circuit in order to extract the average component signal of the signal supplied by said sample and hold circuit wherein said average component signal represents the respiratory rate signal which is supplied by an output of said filter which constitutes the output of said extraction means.

2. The apparatus according to claim 1 further comprising a threshold detector of at least one predetermined amplitude threshold of said respiratory rate signal wherein said detector is connected to an output of said extraction means for extracting the signal representing the respiratory rate and wherein an output of said threshold detector is connected to an alarm in order to trigger said alarm when a difference between said amplitude threshold and the amplitude of the signal representing the respiratory rate exceeds a predetermined value.

3. The apparatus according to claim 2 wherein said amplitude threshold detector includes a means for introducing a delay for delaying the release of said alarm control.

4. An apparatus according to claim 1 further comprising a threshold detector of at least one predetermined frequency threshold of the respiratory rate signal wherein said detector is connected to an output of said extracting means for extracting the signal representing the respiratory rate with an output of said threshold detector being connected to an alarm in order to trigger said alarm when a difference between said frequency threshold and the frequency of said respiratory rate signal exceeds a predetermined value.

5. An apparatus according to claim 1 further comprising a threshold detector of at least one predetermined value representing the product of the amplitude of the respiratory rate signal and the period of said signal wherein said detector is connected to an output of said means for extracting the signal representing the respiratory rate and wherein an output of said threshold detector is connected to an alarm in order to trigger said alarm when the difference between said predetermined threshold value of said product and the value of the product of the amplitude of the respiratory rate signal exceeds a predetermined value.

6. An apparatus according to any one of claims 2-5 further comprising a frequency analyzer connected to the output of said heart pulse detector in order to determine the frequency of the detected pulses wherein said frequency represents said heart rate; and
   a frequency threshold detector having at least one predetermined heart rate frequency threshold wherein the output of said frequency threshold detector is connected to an output of said analyzer in order to supply a signal for releasing an alarm control when the difference between said frequency threshold and the frequency determined by said analyzer exceeds a predetermined frequency value.

7. An apparatus according to claim 6 wherein said heart rate frequency threshold detector includes a means for introducing a delay to the release of said alarm control.

8. An apparatus according to claim 1, wherein said sensor has at least two electrodes located in on a body of a person monitored, in a zone close to the heart of said person.

9. The apparatus according to claim 8, wherein said sensor has a third electrode for establishing a reference potential, said third electrode being located in said zone.

* * * * *